United States Patent [19]

Putsche, Jr. Fred W.

[11] Patent Number: 5,310,725
[45] Date of Patent: May 10, 1994

[54] METHOD OF ERADICATION OF UNDESIRABLE VEGETATION USING FLUORESCEIN DYES

[76] Inventor: Putsche, Jr. Fred W., 517 La Claire Ave., Linthicum Heights, Md. 21090

[21] Appl. No.: 116,366

[22] Filed: Sep. 3, 1993

Related U.S. Application Data

[63] Continuation-in-part of Ser. No. 820,764, Jan. 15, 1992, Pat. No. 5,252,541.

[51] Int. Cl.$^5$ ............................................. A01N 43/16
[52] U.S. Cl. .................................................... 504/297
[58] Field of Search ................ 504/297; 549/223, 224; A01N 43/16

[56] References Cited

U.S. PATENT DOCUMENTS

| | | | |
|---|---|---|---|
| 2,222,225 | 1/1940 | Green | 71/88 |
| 4,500,343 | 2/1985 | Burow, Jr. | 71/76 |
| 4,781,843 | 11/1988 | Baker et al. | 71/67 |

Primary Examiner—Richard L. Raymond
Assistant Examiner—S. Mark Clardy
Attorney, Agent, or Firm—Robert M. Downey

[57] ABSTRACT

A method of eradicating undesirable vegetation including the steps of: preparing a predetermined concentration of fluorescent dye, the dye including a photodynamic pigment which in the presence of oxygen acts as a sensitizer for photo-oxidation in the vegetation; and applying a charge of the dye to soil in the vicinity of the roots of the vegetation, thereby leading to the absorption of the dye by the roots of the vegetation such that the dye reacts with proteins, fatty acids, and lipids at cellular membranes of the vegetation causing membrane lipid peroxidation; and as a result of the reaction, causing the destruction of cells and tissues and the subsequent death of the vegetation.

18 Claims, No Drawings

METHOD OF ERADICATION OF UNDESIRABLE VEGETATION USING FLUORESCEIN DYES

This application is a continuation-in-part application of copending patent application Ser. No. 07/820,764 filed on Jan. 15, 1992;

BACKGROUND OF THE INVENTION

1. Field of the Invention

The present invention relates to a method of eradicating vegetation through the application of a fluorescein dye to the vegetation, thereby resulting in an effective, cost efficient, quick acting and safe means of disposing of undesirable or hazardous vegetation.

2. Description of the Prior Art

The need to eliminate undesirable vegetation is encountered in a vast array of industries at various levels. For instance, undesirable vegetation includes vegetation that the weekend gardener characterizes as weeds. Of greater concern, however, would be vegetation that exhibits uncontrollable, rapid growth such as the fast growing vine Kudzu which takes over telephone poles, power lines, virtually all landscape including trees and anything else in its path. Aside from domestic weeds and other plant life which exhibits uncontrollable growth, undesirable vegetation further includes unlawful vegetation such as the marijuana, coca and poppy plants. For all of these various types of vegetation, it would be highly desirous to have a cost efficient, quick acting, easy-to-apply and nontoxic method of eradication.

The eradication of the marijuana plant by law enforcement officials is of particular importance and difficulty, thereby requiring a new effective eradication means in this industry. Currently, an extensively used method of eradication involves manual removal of the vegetation which has numerous disadvantages. This type of eradication is expensive, time consuming, and most of all dangerous. Manual removal requires the marijuana plants to be cut down and either hauled away to often distant loading trucks outside inaccessible fields, or burned on the growing site. These activities carry with them the dangers of swinging machetes, heat exhaustion, confrontations with poisonous snakes and the need to use large quantities of flamable fuel to burn the green plants. The extensive burning of marijuana fields can lead to uncontrollable brush fires and excessive air pollution. Additionally, cultivation of marijuana plants by growers is a highly profitable business, and many growers arm themselves heavily in order to protect their crops. It is not uncommon for growers in the drug industry to use snipers and high tech booby-traps in an effort to protect their crop and intimidate federal officials.

Another method of eradication often used by the government in its fight against the drug trade as well as farmers, involves the use of herbicides. While nontoxic herbicides are preferable, their general ineffectiveness leads to the more frequent use of toxic herbicides. Unfortunately, these highly toxic herbicides, such as Paraguat, which has been used extensively for the eradication of the marijuana plant, are undetectable by ordinary means once sprayed on the vegetation. Thus, there is nothing to prevent an unscrupulous grower from harvesting the marijuana plants and selling them to unsuspecting buyers even after contamination by Paraquat.

Beyond the drug industry, there is also the concern of using toxic herbicides in the farming and landscape industries. Toxic herbicides are known to contaminate the underground water supply which can have long term detrimental effects to the general population. Additionally, produce which has been treated with toxic herbicides must be carefully washed before human consumption.

In view of the numerous disadvantages of the present methods of vegetation eradication, a safer, more rapid method is needed. Applicant's method is highly effective and overcomes many of the dangers involved with prior methods of eradication. Further, applicant's method, which incorporates the use of a fluorescein dye, facilitates safe and easy application, provides discoloration of the harmful vegetation such that its treatment is highly noticeable, and reacts quickly to kill the vegetation.

Other uses of fluorescein dye have been known as disclosed in U.S. Pat. No. 4,781,843 which recites a process whereby a fluorescein dye is used to control algae growth in open water systems, such as water cooling towers, by absorbing and accordingly blocking the light necessary for photosynthesis, and thereby preventing algae growth. This method does not utilize or suggest direct absorption through the roots of vegetation resulting the death of living plant life.

SUMMARY OF THE INVENTION

The present invention relates to the process of preparing a predetermined concentration of fluorescein dye, and applying a charge of the fluorescein dye, using dispersion means, to the soil in the vicinity of the roots of the vegetation for subsequent absorption thereby, so as to initiate a reaction with proteins, fatty acids, and lipids at cellular membranes of the vegetation. This reaction causes membrane lipid peroxidation, resulting in the death of the vegetation by destruction of the cells and tissues therein.

The main object of the present invention is to provide a process of eradicating unwanted vegetation quickly and easily. More specifically, the purpose is to remove the need for manual eradication and instead apply a charge of a predetermined concentration of dye to the soil surrounding the base of the vegetation by various dispersion means, wherein the reaction of the dye in the cellular membranes of the vegetation cause quick an effective destruction.

Another object of the present invention is to provide a process of eradicating unwanted vegetation which is environmentally friendly, and is safe to animals and humans if subsequent ingestion of the treated vegetation occurs.

Yet another object of the present invention is to provide a method of eradication of unwanted vegetation which reacts quickly to give visible indication of treatment.

These and other objects of the present invention will be more readily apparent from the following description.

DETAILED DESCRIPTION O THE PREFERRED EMBODIMENT

In accordance with the present invention directed to the eradication of unwanted vegetation, a predetermined concentration of fluorescein dye is prepared and subsequently applied to the soil in the vicinity of the roots of the vegetation for absorption thereby.

Fluorescein dyes are preferred for use in the process of the invention and includes D & C Red No. 22 or D & C Red No. 28. D & C Red No. 28 is also know as Eosine Blue, Acid Red 92, Eosine Blush and Phloxine B. These dyes are photodynamic pigments that are inactive in the absence of either light or oxygen, but in the presence of oxygen, they absorb a photon of light and are raised to an excited state whereby they become a sensitizer in the process known as photo-oxidation. The sensitizer interacts with oxygen known as singlet oxygen, which can react with a wide variety of substrates, to give a fully oxidized form of the substrate, and subsequently regenerates and is capable of absorbing an additional photon of light repeating the cycle. The dye, therefore, acts as a true catalyst in the oxidative process, such that a small amount of dye can cause a large amount of oxidative damage.

The site of action of the photodynamic dye is dependent upon what tissues the dye is capable of penetrating and to what molecules it binds. These dyes typically react with proteins, fatty acids, and lipids at cellular membranes causing membrane lipid peroxidation, resulting in death of the cells and related tissues.

For eradicating the marijuana plant, the predetermined concentration of dye and charge includes a weight of six tenths (6/10) pounds of dye dissolved in one gallon of water to form a dye solution. The charge is then applied to the soil in the vicinity of the base of the stem, approximately 4-6 inches from the stem, at a rate of forty (40) milliliters of dye solution per marijuana plant. Thus, one (1) gallon of the dye will treat approximately ninety four (94) plants, and the rate results in the consistent killing of plants up to six feet in height. Further, plants are completely dead in 24-48 hours after application.

Other unwanted vegetation which has been effectively eradicated using the method of the present invention includes dandelions, poison oak, poison ivy, honeysuckle, crabgrass, golden rod and clover. In the treatment of these various types of vegetation, the kill time varied depending upon the size of the vegetation, the amount of dye applied, the intensity of the sun and the duration of exposure time to the sun. In all cases, the dye was applied to the root area at the base of the plants and not on the foilage itself. The mode of action to kill the plant life is the same as with the marijuana plant.

The method of eradication was tested on the above-mentioned plants wherein a mixture of four (4) ounces of the fluorescein dye (D & C Red No. 22 and D & C Red No. 28) to one (1) gallon of water was used. The dosage rate varied between five (5) and twenty (20) milliliters per plant. The results of this test are as follows:

| PLANT | MILLILITERS | KILL TIME IN DAYS |
| --- | --- | --- |
| Poison Oak | 20 | 5 |
| Poison Ivy | 20 | 5 |
| Honeysuckle | 20 | 7 |
| Crabgrass | 10 | 5 |
| Golden Rod | 5 | 3 |
| Clover | 5 | 2 |
| Dandelion | 5 | 2 |

In accordance with the method of the present invention, the charge of dye solution may be applied to the base of the plants using a hand held spraying apparatus or, on a larger scale, it may be applied using aerial spraying means. In the case of aerial spraying, a spraying apparatus could be hung from a helicopter, wherein the apparatus is specifically adapted to disperse the dye mixture at a controlled rate and volume so as to apply the mixture to the base of the plants in an effective manner.

In the preferred embodiment, the dye is of such a nature that it does not stick to the leaves of the vegetation, but rather, drips off down onto the soil for absorption through the roots of the vegetation. Accordingly, dispersion may be performed from a helicopter or like elevated vantage point in a highly effective manner.

While this invention has been described in what is considered to be preferred embodiments thereof, it is recognized that departures may be made within the spirit and scope of the invention which should not therefore be limited except by the following claims and within the doctrine of equivalents.

Now that the invention has been described,
What is claimed is:

1. A method of eradicating unwanted vegetation comprising the steps of:
preparing a dye solution having a predetermined concentration of a regenerative fluorescein dye, said dye being a photodynamic pigment which in the presence of oxygen acts as a sensitizer for photo-oxidation in the vegetation, and
applying a charge of the fluorescein dye solution, using dispersion means to soil in the vicinity of the roots of the vegetation for subsequent absorption thereby, so as to initiate a reaction between the fluorescein dye and proteins, fatty acids, and lipids at a cellular membrane of the vegetation, which thereby causes membrane lipid peroxidation, resulting in the destruction of cell fibers in the vegetation and the subsequent death thereof.

2. The method as recited in claim 1 wherein said fluorescein dye is D & C Red No. 28.

3. The method as recited in claim 1 wherein said fluorescein dye is D & C Red No. 22.

4. The method as recited in claim 1 further comprising the step of dissolving said fluorescein dye in water at approximately 6/10 pounds of said fluorescein dye per 1 gallon of said water to form said dye solution.

5. The method as recited in claim 4 wherein the charge of said fluorescein dye solution is applied at a rate of 40 milliliters of said dye solution per plant.

6. The method as recited in claim 5 wherein said vegetation is the marijuana plant.

7. The method as recited in claim 1 further comprising the step of dissolving said fluorescein dye in water at approximately 4 ounces of said fluorescein dye per 1 gallon of said water to for said dye solution.

8. The method as recited in claim 7 wherein said charge of fluorescein dye solution is applied at a rate of at least 5 milliliters of said dye solution per plant.

9. The method as recited in claim 8 wherein said vegetation is poison oak.

10. The method as recited in claim 8 wherein the vegetation is poison ivy.

11. The method as recited in claim 8 wherein the vegetation is honeysuckle.

12. The method as recited in claim 8 wherein the vegetation is crabgrass.

13. The method as recited in claim 8 wherein the vegetation is golden rod.

14. The method as recited in claim 8 wherein the vegetation is clover.

15. The method as recited in claim 8 wherein the vegetation is dandelion.

16. The method as recited in claim 1 wherein said fluorescein dye solution is applied to the base of the stem of the vegetation.

17. The method as recited in claim 1 wherein said fluorescein dye solution does not stick to leaves of the vegetation.

18. The method as recited in claim 1 wherein said dispersion means includes a helicopter having a spraying apparatus.

* * * * *